(12) United States Patent
Kato

(10) Patent No.: US 11,771,306 B2
(45) Date of Patent: Oct. 3, 2023

(54) IMAGING SYSTEM AND ENDOSCOPE DEVICE

(71) Applicant: OLYMPUS CORPORATION, Hachioji (JP)

(72) Inventor: Shuichi Kato, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 43 days.

(21) Appl. No.: 17/706,182

(22) Filed: Mar. 28, 2022

(65) Prior Publication Data

US 2022/0211253 A1 Jul. 7, 2022

Related U.S. Application Data

(63) Continuation of application No. PCT/JP2019/038740, filed on Oct. 1, 2019.

(51) Int. Cl.
*H04N 5/073* (2006.01)
*A61B 1/00* (2006.01)
(Continued)

(52) U.S. Cl.
CPC .......... *A61B 1/00114* (2013.01); *A61B 1/045* (2013.01); *H04N 5/073* (2013.01);
(Continued)

(58) Field of Classification Search
CPC ...... H04N 25/745; H04N 25/75; H04N 17/00; H04N 17/002; H04N 5/376; H04N 5/073; H04N 7/18; A61B 1/00114; A61B 1/045
(Continued)

(56) References Cited

U.S. PATENT DOCUMENTS

| 8,073,060 B2 * | 12/2011 | Compton | H04N 21/4305 348/521 |
| 8,212,863 B2 * | 7/2012 | Tanaka | A61B 1/00006 348/76 |

(Continued)

FOREIGN PATENT DOCUMENTS

| EP | 3 367 667 A1 | 8/2018 |
| JP | 2005-260913 A | 9/2005 |

(Continued)

OTHER PUBLICATIONS

International Search Report dated Dec. 10, 2019, issued in counterpart International Application No. PCT/JP2019/038740, with English Translation (4 pages).

*Primary Examiner* — Trang U Tran
(74) *Attorney, Agent, or Firm* — WHDA, LLP

(57) ABSTRACT

An embodiment of the present invention is an imaging system in which a camera unit and a control unit are connected by a video signal transmission line and a clock line, and the camera unit and the control unit operate in synchronization with each other by a horizontal synchronization signal and a vertical synchronization signal indicating reading timing of the video signal. The camera unit includes a signal analysis circuit configured to encode information superimposed on a master clock, and encode a register control signal superimposed on the master clock using a camera clock based on timing of the horizontal synchronization signal or the vertical synchronization signal, and write an imaging condition indicated by the register control signal to a register.

7 Claims, 11 Drawing Sheets

(51) Int. Cl.
  *A61B 1/045* (2006.01)
  *H04N 7/18* (2006.01)
  *H04N 17/00* (2006.01)
  *H04N 25/71* (2023.01)
  *H04N 25/75* (2023.01)

(52) U.S. Cl.
  CPC .............. *H04N 7/18* (2013.01); *H04N 17/00* (2013.01); *H04N 17/002* (2013.01); *H04N 25/745* (2023.01); *H04N 25/75* (2023.01)

(58) Field of Classification Search
  USPC ................................................. 348/625, 723
  See application file for complete search history.

(56) References Cited

U.S. PATENT DOCUMENTS

| | | | |
|---|---|---|---|
| 8,654,251 B2 * | 2/2014 | Azzopardi | H04N 23/90 345/475 |
| 10,135,601 B1 * | 11/2018 | Beardsley | H04L 65/764 |
| 10,425,217 B2 * | 9/2019 | Ooishi | H04N 21/4305 |
| 10,595,075 B2 * | 3/2020 | Beardsley | H04N 21/4305 |
| 10,699,666 B2 * | 6/2020 | Jang | G09G 5/18 |
| 2007/0086487 A1 * | 4/2007 | Yasuda | H04J 3/0688 370/503 |
| 2009/0213212 A1 | 8/2009 | Nakamura | |
| 2012/0320174 A1 | 12/2012 | Sato et al. | |
| 2015/0116594 A1 * | 4/2015 | Chuang | H04N 21/4305 348/495 |
| 2018/0288424 A1 * | 10/2018 | LaBosco | H04N 21/24 |
| 2019/0068859 A1 | 2/2019 | Numasawa et al. | |

FOREIGN PATENT DOCUMENTS

| | | |
|---|---|---|
| JP | 2007-37569 A | 2/2007 |
| JP | 2008-80007 A | 4/2008 |
| JP | 2009-201540 A | 9/2009 |
| JP | 2013-453 A | 1/2013 |
| JP | 2013-248277 A | 12/2013 |
| JP | 2017-209184 A | 11/2017 |
| JP | 2019-47297 A | 3/2019 |
| WO | 2017/068899 A1 | 4/2017 |

* cited by examiner

IMAGING SYSTEM AND ENDOSCOPE DEVICE

CROSS-REFERENCE TO RELATED APPLICATIONS

This application is a continuation application based on PCT Patent Application No. PCT/JP2019/038740, filed on Oct. 1, 2019, the entire content of which is hereby incorporated by reference.

BACKGROUND

Technical Field

The present invention relates to an imaging system and an endoscope device.

Background Art

In an imaging system such as an endoscope in which a camera unit with a built-in imager and a control unit for controlling the camera unit are separated from each other via a cable, a plurality of types of signal lines are laid in the cable, which is disclosed in, for example, Japanese Unexamined Patent Application, First Publication No. 2017-209184 (hereinafter referred to as Patent Document 1). In the imaging system described in Patent Document 1, three types of signal lines are laid in the cable. One of the three types transmits a system reference clock from the control unit to the camera unit. Another one transmits a control signal from the control unit to the camera unit. The other is to transmit a video signal from the camera unit to the control unit.

With the promotion of minimally invasive medical procedure in the medical industry due to aging, minimally invasive endoscopes are also required, and reducing the diameter of endoscopes has become an important issue. When pursuing miniaturization of the distal end of the scope, reducing the types of signal lines connecting the camera unit and control unit arranged at the distal end of the scope becomes an important issue.

SUMMARY

The present invention provides an imaging system and an endoscope device capable of reducing the types of signal lines connecting a camera unit and a control unit.

An aspect of the present invention is an imaging system, in which a camera unit and a control unit are connected by a video signal transmission line that transmits a video signal from the camera unit to the control unit and a clock line that transmits a master clock from the control unit to the camera unit, and the camera unit and the control unit operate in synchronization with each other by a horizontal synchronization signal and a vertical synchronization signal indicating a reading timing of the video signal, wherein the camera unit includes an imager configured to generate the video signal; a register configured to be capable of writing and setting an imaging condition of the imager; a camera clock generation circuit configured to synchronize with the master clock and generate a camera clock having a predetermined duty; and a signal analysis circuit configured to encode information superimposed on the master clock, the control unit includes a register control signal transmitter configured to change a duty of the master clock based on a timing of the horizontal synchronization signal or the vertical synchronization signal, to superimpose a register control signal, which indicates the imaging condition of the imager on the master clock and transmits it, using a combination of a first signal having a duty shorter than the camera clock and a second signal having a duty longer than the camera clock, and the signal analysis circuit is configured to encode the register control signal superimposed on the master clock using the camera clock based on the timing of the horizontal synchronization signal or the vertical synchronization signal, and write the imaging condition indicated by the register control signal to the register.

In the imaging system, a transmission time of a high-level signal and a transmission time of a low-level signal by the first signal and the second signal may be substantially the same within a predetermined period.

In the imaging system, true and false of binary numbers constituting the register control signal may each be represented by a combination of the first signal and the second signal, a period of the high-level signal and a period of the low-level signal by the first signal and the second signal constituting the true may be substantially the same, and a period of the high-level signal and a period of the low-level signal by the first signal and the second signal constituting the false may be substantially the same.

In the imaging system, the true and false of the binary numbers constituting the register control signal may be represented by changing a pair order of the first signal and the second signal.

In the imaging system, the signal analysis circuit may include a DFF (D flip-flop) circuit configured to determine the high-level signal or the low-level signal of the register control signal superimposed on the master clock at a timing of a falling edge of the camera clock, a frequency division clock generation circuit configured to divide the camera clock to generate a frequency division clock having a double cycle, and an FF (flip-flop) circuit configured to determine the pair order of the first signal and the second signal and determine the true or the false, based on the high-level signal or the low-level signal determined by the DFF circuit and the frequency division clock.

In the imaging system, the register control signal transmitter may be configured to transmit the register control signal to which an error correction code is added, and the signal analysis circuit may be configured to encode the register control signal, and writes the imaging condition indicated by the register control signal, which has been correctly transmitted, to the register based on the error correction code.

An aspect of the present invention is an endoscope device that includes the imaging system, wherein the camera unit is arranged at a distal end of an insertion part, and the control unit is arranged in a main body.

According to each aspect of the present invention, since the register control signal indicating an imaging condition of the imager can be superimposed on the master clock and transmitted, the types of signal lines connecting the camera unit and the control unit can be reduced.

DETAILED DESCRIPTION OF THE PREFERRED EMBODIMENTS

Figure 1:
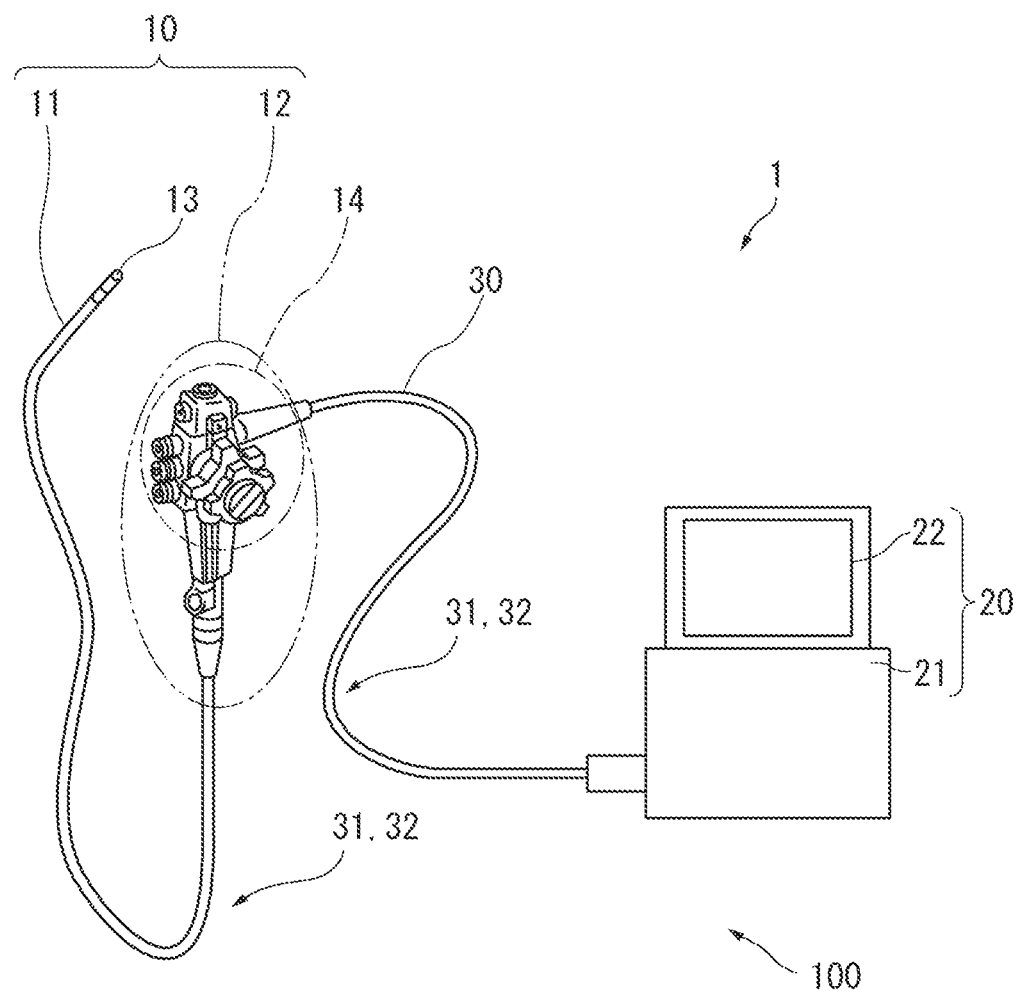
FIG. 1 is a configuration diagram showing a schematic configuration of an endoscope device according to an embodiment of the present invention.

Hereinafter, embodiments of the present invention will be described with reference to the drawings. In each figure, the same reference numerals are used for the same or corresponding configurations, and the description thereof will be omitted as appropriate.

FIG. 1 is a configuration diagram showing a schematic configuration of an endoscope device 1 according to an embodiment of the present invention. In FIG. 1, the endoscope device 1 includes an endoscope scope unit 10 and a main body 20. The endoscope device 1 is, for example, an endoscope device for a digestive organ.

The endoscope scope unit 10 includes an insertion part 11 and an operation part 12. The insertion part 11 includes a camera unit 13 at the distal end thereof. Further, the main body 20 includes a control unit 21 and a color monitor 22. The operation part 12 and the control unit 21 are connected by a universal cord 30. A configuration in which the camera unit 13 and the control unit 21 are combined is one aspect of an imaging system 100 in the present invention. The endoscope device 1 shown in FIG. 1 is a device including the imaging system 100, in which the camera unit 13 is arranged at the distal end of the insertion part 11 and the control unit 21 is arranged at the main body 20.

In the endoscope device 1, the operation part 12 and the light source device (not shown) provided in the main body 20 are connected by a light guide (not shown) that transmits light to irradiate a portion to be observed. In the endoscope scope unit 10, the insertion part 11 is inserted into the digestive organ or the like in the body of the person to be inspected, and an image of a site to be observed (hereinafter referred to as "observation site") is imaged. At this time, the observation site is irradiated with illumination light guided by a light guide (not shown) from the distal end of the insertion part 11. The endoscope scope unit 10 outputs (transmits) a video signal according to the image of the observation portion captured by the camera unit 13 to the control unit 21 by a signal line (video signal transmission line 32) in the insertion part 11, the operation part 12, and the universal cord 30.

The operation part 12 is a support unit that controls the operation of the insertion part 11 and the camera unit 13 by being operated by, for example, an operator (for example, a doctor performing gastrointestinal surgery). The operation part 12 includes an operation switch 14 for controlling the direction in which the distal end of the insertion part 11 is inserted into the body and the imaging in the endoscope device 1. The operation switch 14 outputs, for example, an instruction signal for instructing the observation portion to be photographed to the control unit 21 via the operation part 12 and the universal cord 30 in response to the operation of the operator.

The control unit 21 controls the camera unit 13, inputs the video signal output from the camera unit 13, performs predetermined image processing, and displays the processed image on the color monitor 22. The control unit 21 transmits a control signal for controlling the camera unit 13 to the camera unit 13 through the universal cord 30, the operation part 12, and the signal line (clock line 31) in the insertion part 11.

The color monitor 22 displays an image including an observation portion corresponding to an image signal input from the control unit 21. The color monitor 22 is a display device such as a liquid crystal display or an organic electroluminescence display.

Figure 2:
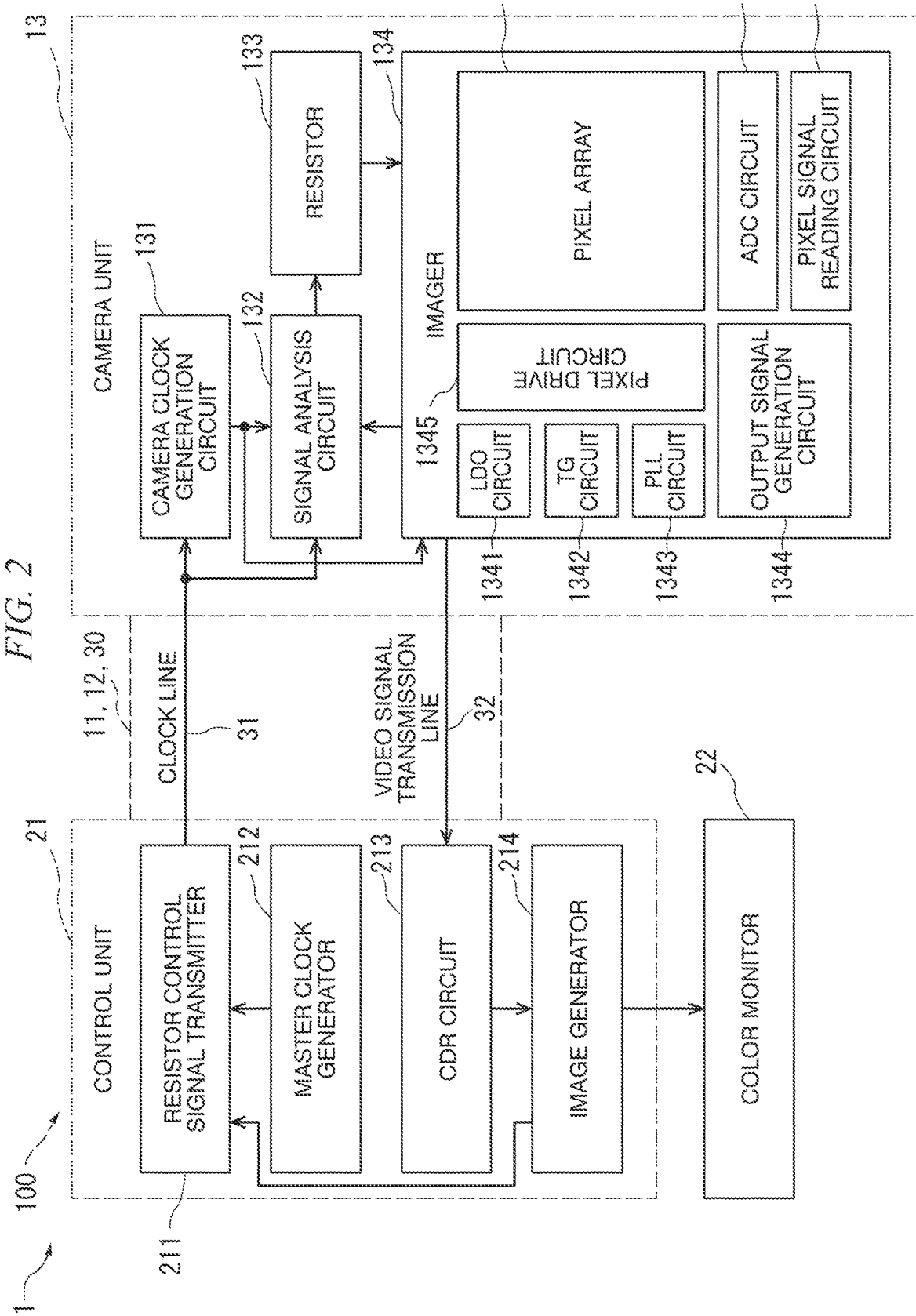
FIG. 2 is a block diagram showing a schematic configuration of a camera unit 13 and a control unit 21 shown in FIG. 1.
Figure 3:
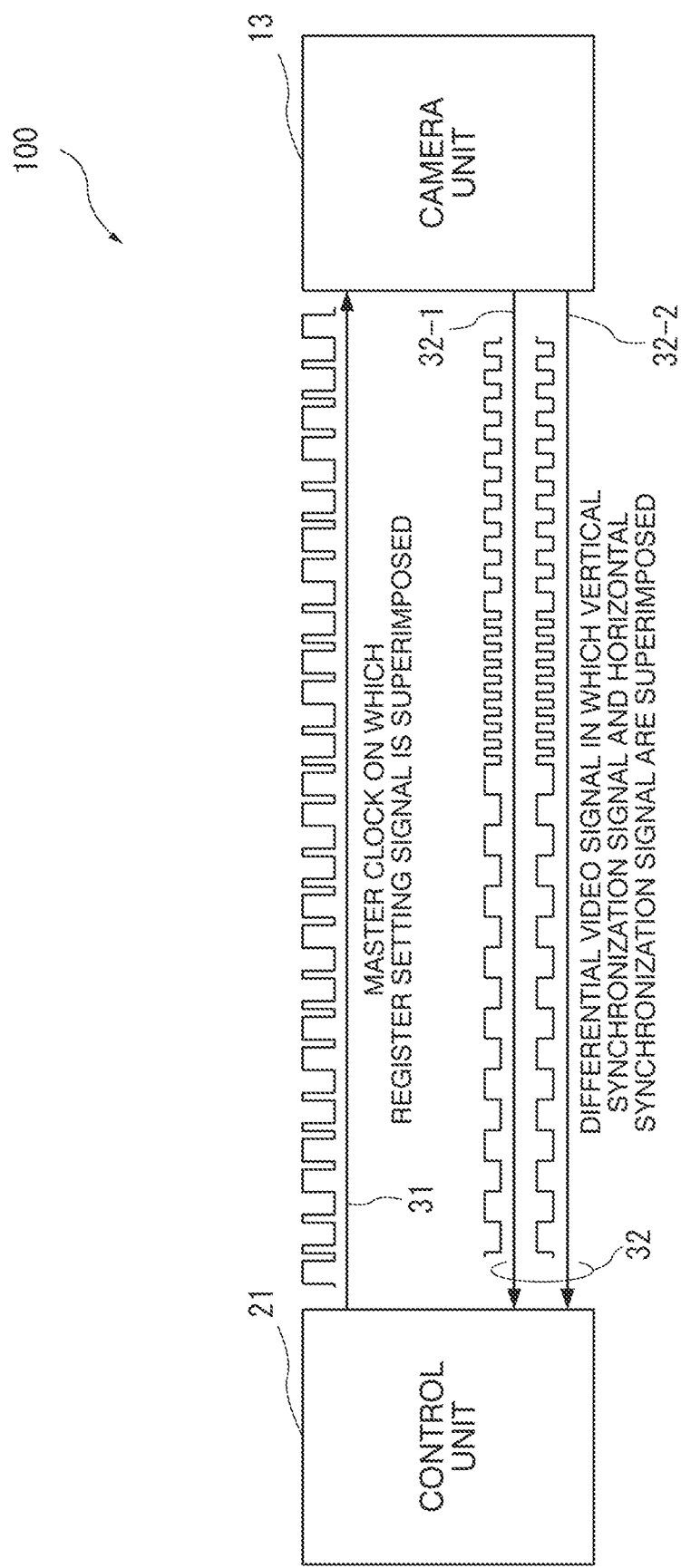
FIG. 3 is a schematic diagram explaining an example of a signal transmitted by a clock line 31 and a video signal transmission line 32 shown in FIG. 2.

FIG. 2 is a block diagram showing a schematic configuration of the camera unit 13 and the control unit 21 shown in FIG. 1. The camera unit 13 and the control unit 21 are connected by a clock line 31 that transmits a master clock from the control unit 21 to the camera unit 13 and a video signal transmission line 32 that transmits a video signal from the camera unit 13 to the control unit 21. The master clock is a common reference clock in the control unit 21 and the camera unit 13. As shown in FIG. 3, the master clock transmitted from the control unit 21 to the camera unit 13 via the clock line 31 is a master clock on which a register-setting signal described later is superimposed. FIG. 3 is a schematic diagram explaining an example of a signal transmitted by the clock line 31 and the video signal transmission line 32 shown in FIG. 2. In the imaging system 100, the horizontal synchronization signal and the vertical synchronization signal indicating the reading timing of the video signal operate in synchronization between the camera unit 13 and the control unit 21. That is, in the imaging system 100, the camera unit 13 and the control unit 21 operate in synchronization with each other by the horizontal synchronization signal and the vertical synchronization signal indicating the reading timing of the video signal.

The clock line 31 and the video signal transmission line 32 are laid in the insertion part 11, the operation part 12, and the universal cord 30. The camera unit 13 and the control unit 21 are connected to a power supply line (not shown) by a GND (ground) line, and DC power is supplied from the control unit 21 to the camera unit 13.

The camera unit 13 has a camera clock generation circuit 131, a signal analysis circuit 132, a register 133, and an imager 134. The configuration of the camera unit 13 is not limited to the form shown in FIG. 2, and for example, the camera clock generation circuit 131, the signal analysis circuit 132, the register 133, and the imager 134 may be integrally configured.

The camera clock generation circuit 131 synchronizes with the master clock received from the control unit 21 via the clock line 31, and generates a camera clock having a predetermined duty (for example, 50%) in the same cycle as the master clock. An operation example of this camera clock generation circuit 131 will be described later. In the present embodiment, the duty is also referred to as a duty ratio, and is a ratio of, for example, a high-level period to a period of one cycle consisting of a high level and a low level.

The signal analysis circuit 132 is a circuit that encodes information (register-setting signal) superimposed on the master clock received via the clock line 31. The signal analysis circuit 132 encodes the register control signal superimposed on the master clock using the camera clock based on the timing of the horizontal synchronization signal or the vertical synchronization signal, and writes the imaging conditions indicated by the register control signal to the register 133.

The register 133 is a storage circuit that can write and set the imaging conditions of the imager 134 based on the information (register-setting signal) encoded by the signal analysis circuit 132. That is, the register 133 stores various setting values (parameters) for defining the operation of the imager 134 transmitted from the control unit 21. The register 133 stores the setting values (parameters) related to the shooting function of the imager 134, such as the exposure time (accumulation time) of the imager 134, the frame rate of the moving image, the image size (number of pixels) representing the size of the image, and the reading method when outputting the video signal. Further, the register 133 stores the setting values (parameters) for controlling the operation and execution of functions other than shooting provided in the imager 134, such as a vertical blanking period (number of horizontal synchronization signals), a horizontal blanking period (number of master clock signals), and setting values (parameters) for generating a synchronization signal (vertical synchronization signal and horizontal synchronization signal).

The imager 134 is a circuit that generates a video signal based on the captured image, and is a CMOS (Complementary Metal-Oxide-Semiconductor) image sensor in the present embodiment. The imager 134 includes an LDO circuit 1341, a TG circuit 1342, a PLL circuit 1343, an output signal generation circuit 1344, a pixel drive circuit 1345, a pixel array 1346, an ADC circuit 1347, and a pixel signal-reading circuit 1348.

The pixel array 1346 is composed of a plurality of light-receiving elements arranged in the row and column directions, and converts the signal (pixel signal) of each light receiving element into an electric signal. The pixel drive circuit 1345 is a circuit that drives (resets, reads, etc.) the selected row. The ADC (Analog-to-Digital Converter) circuit 1347 is a circuit that converts an analog pixel signal read by the pixel drive circuit 1345 into a digital signal and writes it to a line memory. The pixel signal-reading circuit 1348 has a line memory, and is a circuit that serializes a parallel digital pixel signal of all rows×all bits written in the line memory by the ADC circuit 1347 and outputs it in chronological order. The output signal generation circuit 1344 processes the digital pixel signal from the pixel signal-reading circuit 1348, embeds a flag signal capable of recognizing the timing of the vertical synchronization signal and the horizontal synchronization signal between the serial digital pixel signals after signal processing, and adds modulation (for example, 8b/10b coding) so that the synchronous clock can be reproduced in the CDR circuit described later. The PLL (Phase-Locked Loop) circuit 1343 is a circuit that synchronizes with the camera clock generated by the camera clock generation circuit 131 and generates a plurality of clocks used to drive the imager 134. The TG (timing generator) circuit 1342 is a circuit that generates a plurality of timing signals (including a vertical synchronization signal and a horizontal synchronization signal) that drive the imager 134 based on the information written in the register 133. The LDO circuit 1341 is a circuit that generates a voltage signal at a level necessary for driving the camera unit 13 from a power supply signal (DC power from the control unit 21 to the camera unit 13) from the control unit 21.

Figure 4:
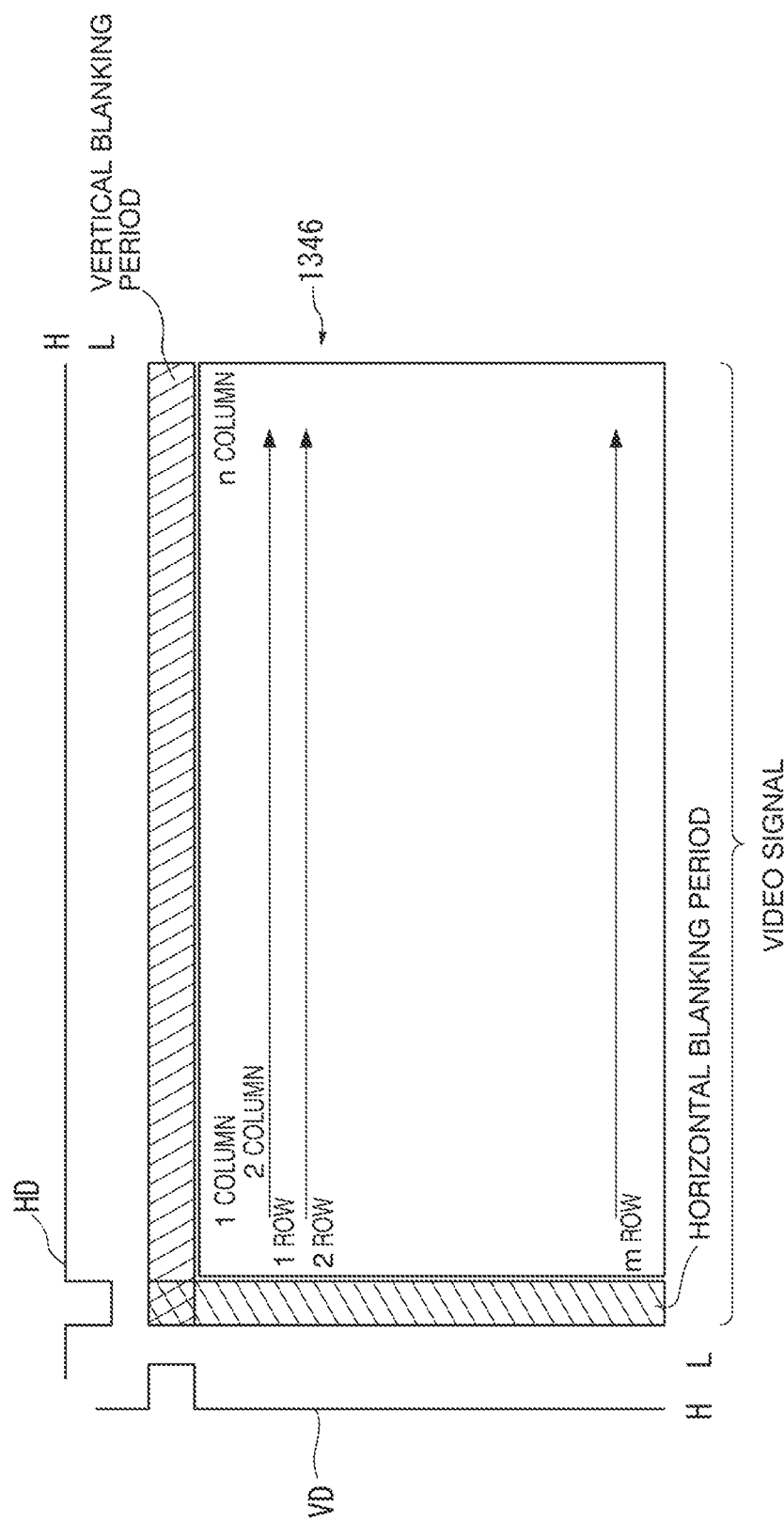
FIG. 4 is a schematic diagram explaining a configuration example of a video signal in an imaging system 100 shown in FIG. 2.

Here, an example of output operation of the imager 134 will be described with reference to FIG. 4. FIG. 4 is a schematic diagram explaining a configuration example of a video signal in the imaging system 100 shown in FIG. 2. FIG. 4 shows an example of a video signal in which information representing a vertical synchronization signal and a horizontal synchronization signal is combined with each pixel signal generated by the pixel array 1346 for one frame (one image). In the vertical synchronization signal VD and the horizontal synchronization signal HD shown in FIG. 4, a high level="H" level indicates a period in which the video signal is valid as a moving image, and a low level="L" level indicates a period in which the video signal is invalid as a moving image, that is, a blanking period (vertical blanking period or horizontal blanking period).

In each frame, the pixel drive circuit 1345 first reads the pixel signal of the first line, the ADC circuit 1347 converts the read analog pixel signal of the first line into a digital pixel signal, and writes the data to the line memory of the pixel signal reading circuit 1348. The output signal generation circuit 1344 outputs a serial signal in which the data of all columns of the line memory are arranged after the flag signal (the recognition signal at the beginning of the line and the recognition signal of which line of the image frame). During the output of the first line, the pixel drive circuit 1345 reads the pixel signal of the second line, and the ADC circuit 1347 converts the read analog pixel signal of the second line into a digital pixel signal. The output signal generation circuit 1344 outputs the flag signal of the second line when the output of the first line is completed, and while the flag signal is being output, the ADC circuit 1347 writes the data of the pixel signal converted into the digital signal to the line memory. Then, the output signal generation circuit 1344 outputs a serial signal in which the data of all columns of the line memory are arranged after outputting the flag signal of the second line. This flow is performed in order for each row of each pixel, and after the end of all rows, the same processing is performed again from the first row after a vertical blanking period (a period of rows without data) for adjusting the frame rate. The number of lines to be set in this vertical blanking period is written in the register 133, and the TG circuit 1342 operates the pixel drive circuit 1345, the ADC circuit 1347, and the output signal generation circuit 1344 according to the timing. The TG circuit 1342 controls a plurality of timing signals that drive the imager 134, and also controls the timing of the vertical blanking period and the horizontal blanking period (the period of the column without data) which is the output period of the flag signal, thereby generating a vertical synchronization signal or a horizontal synchronization signal to output to the signal analysis circuit 132. The output signal generation circuit 1344 finally converts the output video signal into a serial signal of the 8b/10b coding method, and outputs it to, for example, two signal lines 32-1 and 32-2 constituting the video signal transmission line 32 with a differential signal as shown in FIG. 3. In this case, the video signal transmitted to the signal line 32-1 and the signal line 32-2 is a differential video signal in which a vertical synchronization signal and a horizontal synchronization signal are superimposed.

In the above operation, for example, when the digital pixel signal is 12 bits, if 4 bits of "0000" are added to the upper level to make a 16 bit digital pixel signal, "1" does not continuously exceed 16 in the digital video signal. In this case, "11111111_11111111" is data that does not exist in the video signal, and this can be used as the recognition signal at the beginning of the line. In the output signal generation circuit 1344, the 16 bits following the recognition signal ("111111111_111111111") at the beginning of this line is used as the recognition signal of which line of the image frame, and it is possible to write the number of lines of the frame in binary.

On the other hand, in FIG. 2, the control unit 21 has a register control signal transmitter 211, a master clock generator 212, a CDR (Clock Data Recovery) circuit 213, and an image generator 214. Further, the control unit 21 includes a power supply circuit (not shown) that supplies DC power to the camera unit 13.

The master clock generator 212 generates a master clock and outputs it to the register control signal transmitter 211.

The register control signal transmitter 211 superimposes the register control signal indicating the imaging condition of the imager 134 on the master clock and transmits it as the master clock, by the combination of the first signal having a duty shorter than the camera clock and the second signal having a duty longer than the camera clock, by changing the duty of the master clock based on the timing of the horizontal synchronization signal or the vertical synchronization signal included in the video signal transmitted from the camera unit 13 via the video signal transmission line 32. If the register control signal is transmitted regardless of the horizontal synchronization signal or the vertical synchronization signal timing, the camera unit 13 side does not know the encoding start timing of the register control signal. Therefore, in the present embodiment, a register control signal is transmitted based on a predetermined timing of a horizontal synchronization signal or a vertical synchronization signal synchronized between the control unit 21 and the camera unit 13, so that the camera unit 13 side can start encoding at the same timing.

Figure 5:
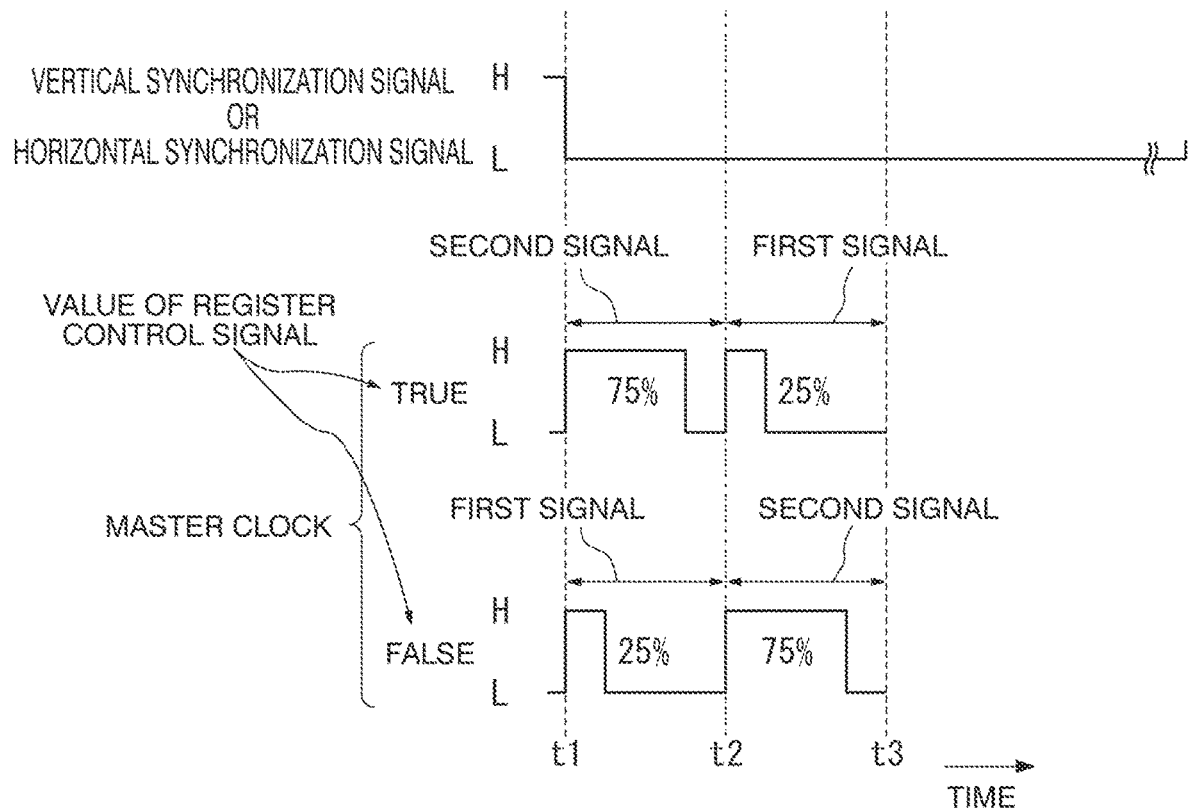
FIG. 5 is a timing chart showing an operation example of a register control signal transmitter 211 shown in FIG. 2.
Figure 6:
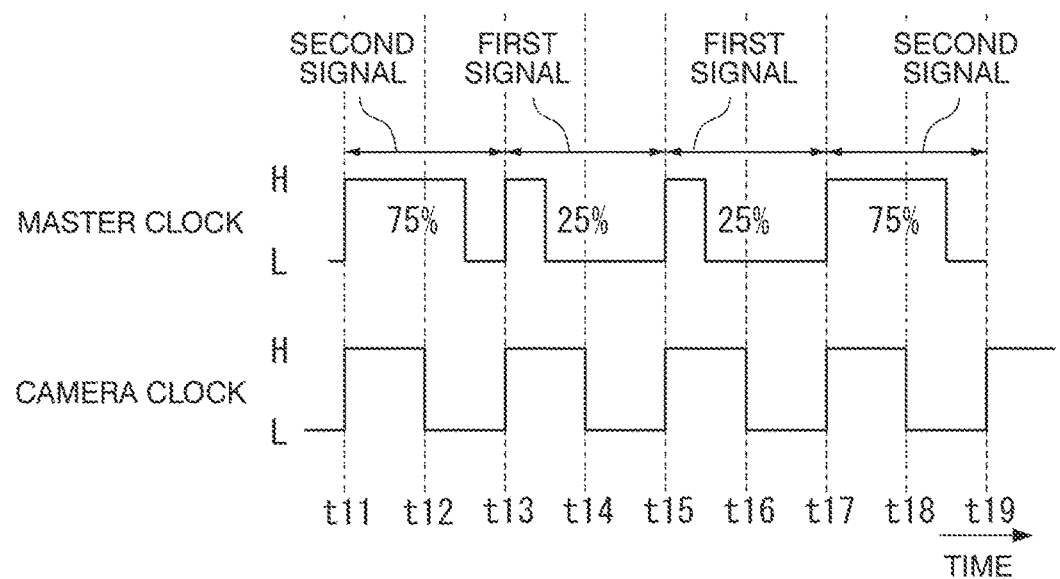
FIG. 6 is a timing chart showing an operation example of a camera clock generation circuit 131 shown in FIG. 2.

When the duty of the master clock and the duty of the camera clock are 50%, as shown in FIGS. 5 and 6, for example, the duty of the first signal can be 25% and the duty of the second signal can be 75%. FIG. 5 is a timing chart showing an operation example of the register control signal transmitter 211 shown in FIG. 2. FIG. 6 is a timing chart showing an operation example of the camera clock generation circuit 131 shown in FIG. 2.

FIG. 5 shows, in order from the top, a horizontal synchronization signal or a vertical synchronization signal (horizontal synchronization signal or vertical synchronization signal output by the image generator 214) included in the video signal output by the camera unit 13, and a master clock generated by the register control signal transmitter 211. In FIG. 5, when the master clock is a pair signal that includes the second signal of time t1 to time t2 and the first signal of time t2 to time t3 in order, the binary number "true"="1" (or logic "true"=logic "1") is represented, and when the master clock is a pair signal that includes the first signal of time t1 to time t2 and the second signal of time t2 to time t3 in order, the binary number "false"="0" (or logical "false"=logical "0") is represented, so that a register control signal is composed of a combination of binary numbers "true" and "false".

In the example shown in FIG. 5, the generation of the register control signal by changing the duty of the master clock is started at the same timing (time t1) as the start edge (from high level to low level) of the horizontal synchronization signal or the vertical synchronization signal. However, the generation of the register control signal by changing the duty of the master clock may be started at a timing about a predetermined clock from the start edge of the horizontal synchronization signal or the vertical synchronization signal. Further, in the camera unit 13 and the control unit 21, the horizontal synchronization signal and the vertical synchronization signal are signals that operate in synchronization with the master clock, and in the present embodiment, the timing when the horizontal synchronization signal and the vertical synchronization signal become active (become low level) corresponds to the timing when the master clock rises from the low level to the high level (high edge).

Further, in the example shown in FIG. 5, the register control signal transmitter 211 sets the timing of the high edge of the master clock to a constant cycle, and changes whether the timing of the low edge is late or early, that is, whether the duty is small or large for each clock, to generate a combination of the first signal and the second signal. In the example shown in FIG. 6, the camera clock generation circuit 131 inputs the master clock, and generates the camera clock so as to change from the low level to the high level in synchronization with the high edge of the master clock (time t11, t13, t15, t17), and change from the high level to the low level so that the duty is 50% (time t12, t14, t16, t18). In this case, the camera clock generation circuit 131 generates a camera clock having the same period and phase as the master clock and a duty of 50% with reference to the timing of the high edge of the master clock generated by the master clock generator 212 of the control unit 21. The camera clock generation circuit 131 can be configured as, for example, a PLL circuit, or can be configured to be included in the PLL circuit 1343.

The reason the register control signals "true" and "false" are composed of the combination of the first signal and the second signal is as follows. That is, if the first signal is "true" and the second signal is "false" independently of each other, for example, when the transmission time of the high-level signal becomes significantly longer than the transmission time of the low-level signal due to the continuation of the second signal, the potential of the master clock line may be biased to the high level, which may interfere with signal transmission. On the contrary, when the transmission time of the low-level signal becomes significantly longer than the transmission time of the high-level signal due to the continuation of the first signal, the potential of the master clock line is biased to the low level.

Therefore, in the present embodiment, the binary numbers "true" (="1") and "false" (="0") constituting the register control signal are each determined by the combination of the first signal and the second signal, and the first signal and the second signal are set so that the transmission time of the high-level signal and the transmission time of the low-level signal in the period in which the first signal and the second signal are combined are substantially the same. Further, the transmission time of the high-level signal and the transmission time of the low-level signal by the first signal and the second signal constituting the binary number "true" are made substantially the same, and the transmission time of the high-level signal and the transmission time of the low-level signal by the first signal and the second signal constituting the binary number "false" are substantially the same.

The "true" and "false" constituting the register control signal are not limited to the combination of each one of the first signal and the second signal, and may be composed of the combination of three or more first signals and the second signal. For example, when one "true" is represented as "first signal, first signal, second signal", the duties of the first signal and the second signal are adjusted so that the transmission time of the high-level signal and the transmission time of the low-level signal by "first signal, first signal, second signal" are substantially the same. As a result, it is possible to prevent the potential of the clock line 31 from being biased even when the "true" and the "false" constituting the register control signal are continuous.

Further, the "true" and "false" constituting the register control signal may each be associated with either one of the first signal and the second signal. For example, the first signal may be "true" and the second signal may be "false". In this case, for example, the duty of the camera clock is set to about 50%, the duty of the first signal is set to a value smaller than 50%, which is close to 50%, and the duty of the second signal is set to a value larger than 50%, which is close to 50%. so that, for example, even when "true" is continuous, it is possible to prevent the potential of the clock line 31 from being greatly biased. Further, an error correction code using a checksum, a parity check, or the like can be added to the register control signal in addition to the imaging conditions written in the register 133. In this case, the signal analysis circuit 132 can confirm whether the register control signal is correctly transmitted by using the error stop code, and can write only the imaging condition indicated by the correctly transmitted register control signal to the register.

As described above, in the present embodiment, the transmission time of the high-level signal and the transmission time of the low-level signal by the first signal and the second signal are substantially the same within a predetermined period. Further, the binary numbers "true" and "false" constituting the register control signal are each represented by the combination of the first signal and the second signal, the period of the high-level signal and the period of the low-level signal due to the sum of the first signal and the second signal constituting "true" are substantially the same, and the period of the high-level signal and the period of the low-level signal due to the sum of the first signal and the second signal constituting the "false" are substantially the same. Further, the binary numbers "true" and "false" constituting the register control signal are represented by changing the pair order of the first signal and the second signal, and are expressed so that the master clock can be restored from the signal obtained by superimposing the register control signal on the master clock. In the present embodiment, the register control signal is transmitted by changing the duty of the master clock on the clock line 31, and the dedicated line for transmitting the register control signal can be omitted. Therefore, it is possible to prevent an unintended register control signal from being transmitted from the outside via a dedicated line and being written to the register, thus improving security and being suitable for applications such as surveillance cameras.

Further, the register control signal coding method according to the present embodiment is similar to the Manchester coding method in the following points. That is, the register control signal coding method according to the present embodiment is similar to Manchester coding in that the same level is not continuous in a plurality of consecutive binary data, the clock signal can be restored from the coded data, and the transition at the start and end of one cycle (1 symbol) does not indicate data.

Further, in the control unit 21 shown in FIG. 2, the CDR circuit 213 receives the video signal, generates a clock having the same period as the differential video signal (for example, a clock of 400 MHz if the differential video signal is 400 Mbps) from the differential video signal of the 8b/10b coding method, detects the logic of the differential video signal (pixel signal sandwiching the flag signal) at the same clock, and decodes (performs 10b/8b conversion) the same pixel signal into a signal before 8b/10b encoding and outputs the signal.

The image generator 214 receives the pixel signal sandwiching the flag signal from the CDR circuit 213, generates a video signal (a signal composed of a horizontal synchronization signal, a vertical synchronization signal, and a pixel signal synchronized with the horizontal synchronization signal), outputs a horizontal synchronization signal or a vertical synchronization signal to the register control signal transmitter 211, performs predetermined image processing as necessary, and outputs the output to the color monitor 22.

Figure 7:
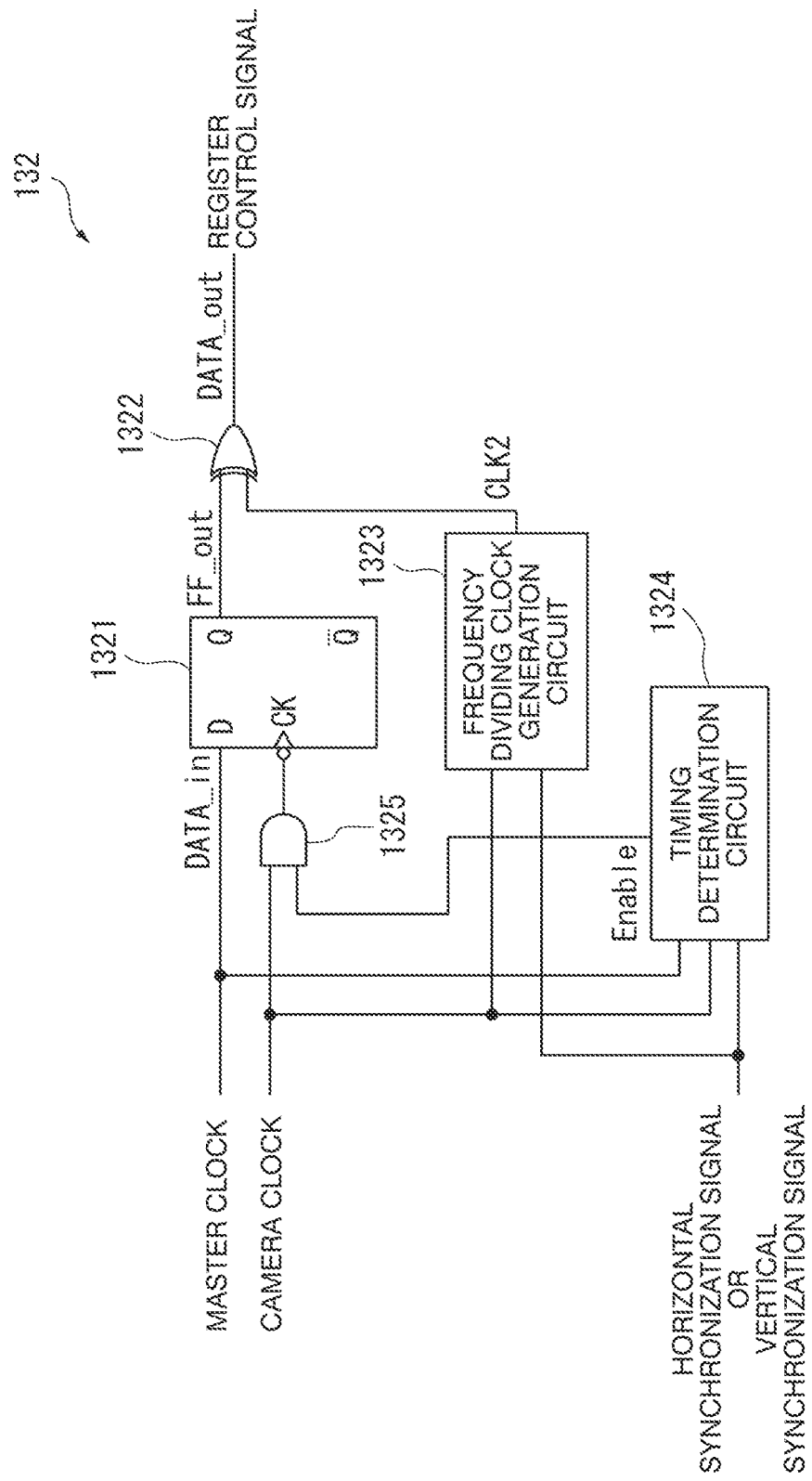
FIG. 7 is a block diagram showing a configuration example of the signal analysis circuit 132 shown in FIG. 2.
Figure 8:
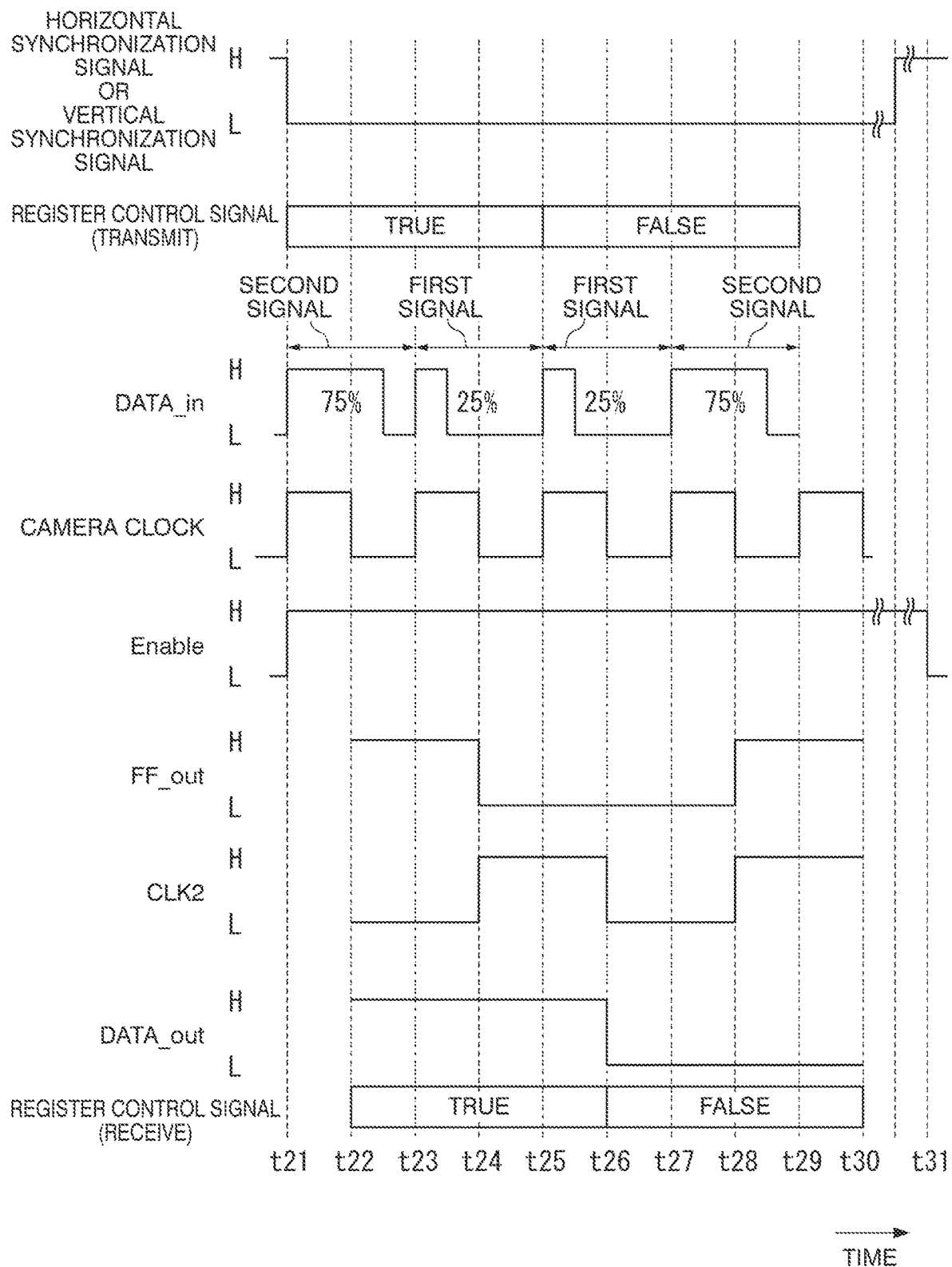
FIG. 8 is a timing chart showing an operation example of a signal analysis circuit 132 shown in FIG. 7.
Figure 9:
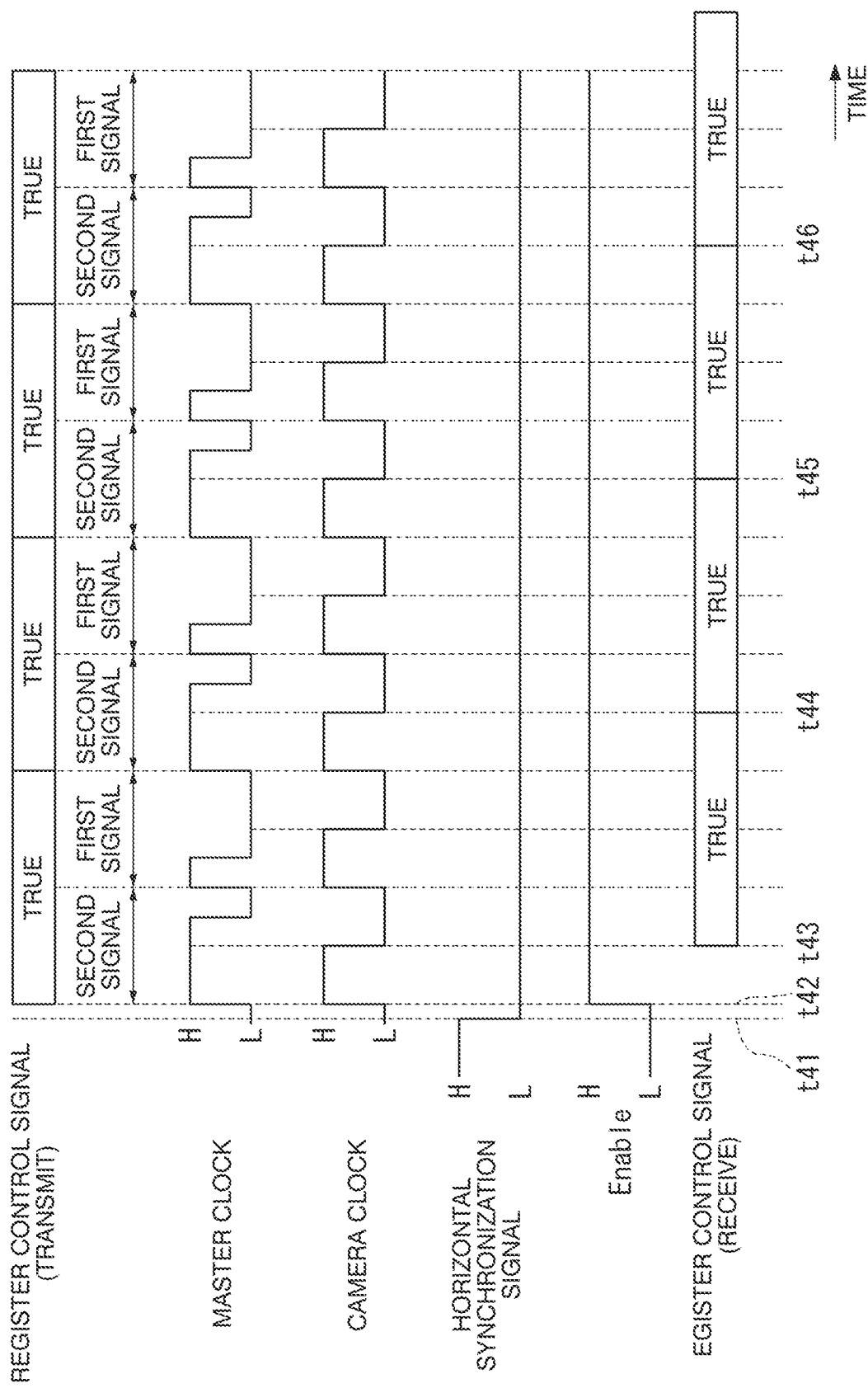
FIG. 9 is a timing chart showing an operation example of the signal analysis circuit 132 shown in FIG. 7.
Figure 10:
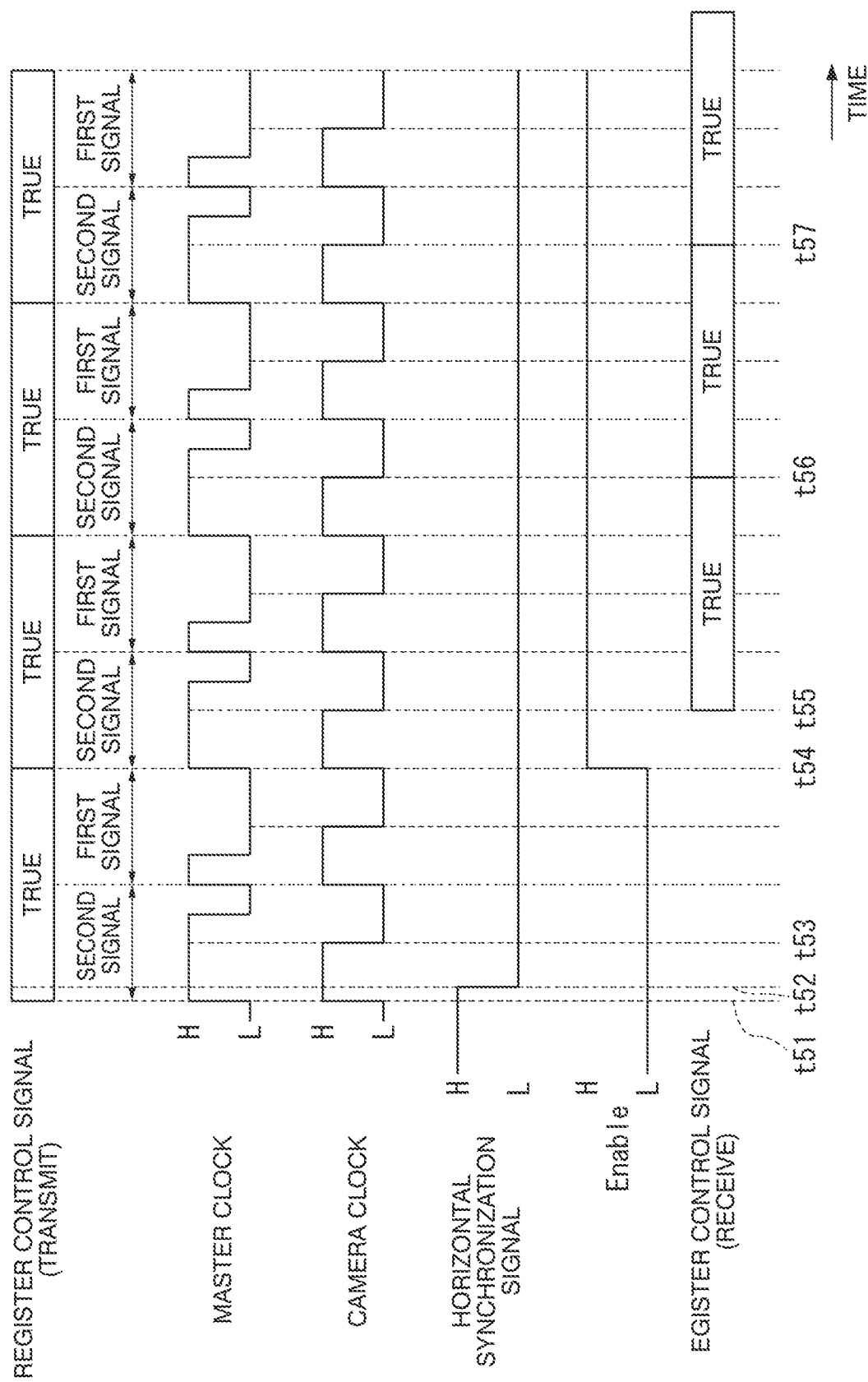
FIG. 10 is a timing chart showing an operation example of the signal analysis circuit 132 shown in FIG. 7.
Figure 11:
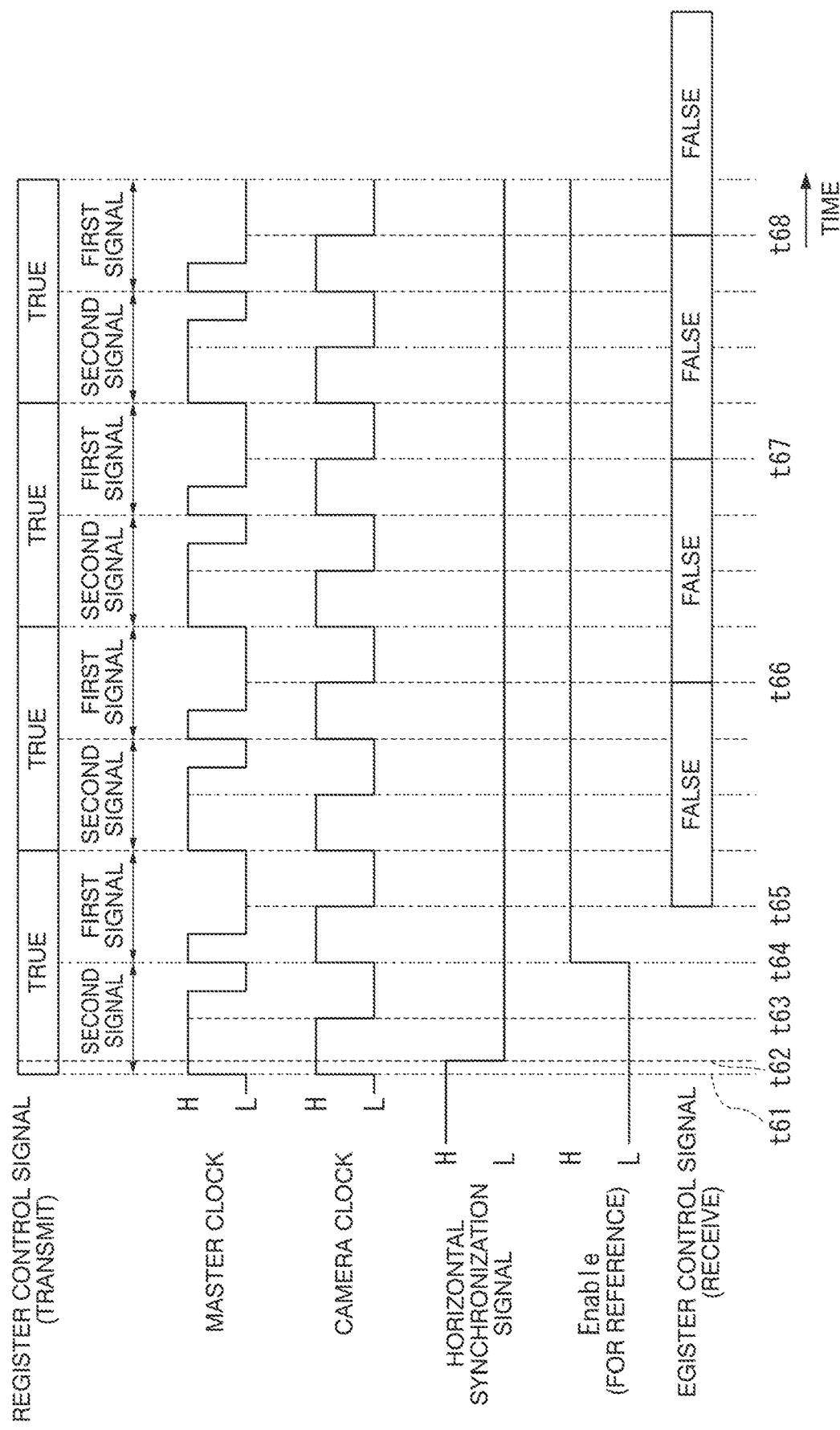
FIG. 11 is a timing chart explaining an operation example of the signal analysis circuit 132 shown in FIG. 7.

Next, the signal analysis circuit 132 shown in FIG. 2 will be described with reference to FIGS. 7 to 11. FIG. 7 is a block diagram showing a configuration example of the signal analysis circuit 132 shown in FIG. 2. FIGS. 8 to 10 are timing charts showing an operation example of the signal analysis circuit 132 shown in FIG. 7. FIG. 11 is a timing chart explaining an operation example of the signal analysis circuit 132 shown in FIG. 7 by showing a comparative example.

In the configuration example shown in FIG. 7, the signal analysis circuit 132 includes a DFF (D flipflop) circuit 1321, an XOR (exclusive OR) circuit 1322, a frequency-dividing clock generation circuit 1323, a timing determination circuit 1324, and an AND (logical product) circuit 1325.

The DFF circuit 1321 inputs the master clock as a signal DATA_in to the input terminal D, inputs the output of the AND circuit 1325 to the low edge clock input terminal CK, and outputs the output signal FF_out from the output terminal Q to one of the input terminals of the XOR circuit 1322. The AND circuit 1325 inputs the camera clock to one input terminal, and inputs the output signal Enable of the timing determination circuit 1324 to the other input terminal. A master clock, a camera clock, and a horizontal synchronization signal or a vertical synchronization signal are input to the timing determination circuit 1324. The frequency-dividing clock generation circuit 1323 inputs the camera clock and the horizontal synchronization signal or the vertical synchronization signal, generates a clock CLK2 having a frequency of half the camera clock with reference to the horizontal synchronization signal or the vertical synchronization signal, and outputs the clock CLK2 to the other input terminal of the XOR circuit 1322. The XOR circuit 1322 outputs a register control signal (binary serial signal) as a signal DATA_out.

The timing determination circuit 1324 determines an effective timing (period) in which the register control signal is superimposed on the master clock, and as shown in FIG. 8, if the horizontal synchronization signal or the vertical synchronization signal changes from the high level to the low level, when the camera clock changes from the low level to the high level (time t21), the timing determination circuit 1324 becomes high level, and after a predetermined time elapses (time t31), the timing determination circuit 1324 outputs an enable signal at the low level. The enable signal represents a valid timing at the high level. The AND circuit 1325 causes the camera clock to be input to the input terminal CK when the signal Enable is at the high level, and does not cause the camera clock to be input to the input terminal CK when the signal Enable is at the low level.

Further, the frequency-dividing clock generation circuit 1323 generates a clock (CLK2) having a frequency of ½ of the camera clock that switches to Low at the timing of the first low edge of the camera clock that appears after the low edge of the horizontal synchronization signal or the vertical synchronization signal. That is, as shown in FIG. 8, if the horizontal synchronization signal or the vertical synchronization signal changes from the high level to the low level, the frequency-dividing clock generation circuit 1323 becomes the low level when the camera clock changes from the high level to the low level (time t22), and then outputs a clock CLK2 that changes at a cycle twice that of the camera clock (clock that changes from the low level to the high level at time t24, from the high level to the low level at time t26, and from the low level to the high level at time t28).

As described above, the signal analysis circuit 132 shown in FIG. 7 includes the DFF circuit 1321 that determines the high-level signal or the low-level signal of the register control signal superimposed on the master clock at the timing of the falling edge of the camera clock, the frequency-dividing clock generation circuit 1323 that divides the camera clock to generate a clock CLK2 (divided clock) with a double cycle, and the XOR circuit 1322 (FF (flip-flop) circuit) that determines the pair order of the first signal and the second signal based on the high-level signal or the low-level signal determined by the DFF circuit 1321 and the clock CLK2 (divided clock) to determine "true" or "false".

FIG. 8 shows an example in which the control unit 21 continuously superimposes and outputs the binary numbers "true" (="1") and "false" (="0") on the master clock as register control signals after the falling of the horizontal synchronization signal or the vertical synchronization signal (time t21). In FIGS. 8 to 11, the register control signal transmitted by the control unit 21 side is shown as a "register control signal (sending)", and the register control signal recognized by the camera unit 13 side is shown as a "register control signal (receiving)". As shown in FIG. 5, the master clock is assumed to be "true" for the combination of the second signal and the first signal in this order, and "false" for the combination of the first signal and the second signal in this order.

Further, in the example shown in FIG. 8, the signal DATA_in, which is the master clock, is a second signal from time t21 to time t23, a first signal from time t23 to time t25, a first signal from time t25 to time t27, and a second signal from time t27 to time t29. The signal Enable becomes the high level (time t21) when the horizontal synchronization signal or the vertical synchronization signal is the low level and the camera clock is the high level, and becomes the low level at the time t31 after a predetermined time.

The signal FF_out becomes the level of the signal DATA_in (high level) when the camera clock changes from the high level to the low level at time t22, and becomes the level of the signal DATA_in (low level) when the camera clock changes from the high level to the low level at time t24. Further, the signal FF_out remains at the signal DATA_in level (low level) when the camera clock changes from the high level to the low level at time t26, and becomes the level of the signal DATA_in (high level) when the camera clock changes from the high level to the low level at time t28.

The signal DATA_out has a high level from time t22 to time t26 and a low level from time t26 to time t30 based on the signal FF_out and clock CLK2. In this case, the signal DATA_out indicates that the register control signal is "true" (="1") from time t22 to time t26 and "false" (="0") from time t26 to time t30.

As described above, the DFF circuit 1321 determines that the signal DATA_in is the second signal if it shows the high level and determines that the signal DATA_in is the first signal if it shows the low level at the falling timing of the camera clock. Then, the XOR circuit 1322 determines the pair order of the first signal and the second signal based on the high-level signal or the low-level signal determined by the DFF circuit 1321 and the clock CLK2 (divided clock), and operates as an FF (flip-flop) circuit that determines the "true" or "false" of a binary number. In this case, the signal DATA_out output from the XOR circuit 1322 becomes a signal ("register control signal (receiving)") that restores the register control signal ("register control signal (sending)") superimposed on the signal DATA_in, which is the master clock, with a delay of half a cycle of the camera clock.

Next, a modified example of the operation of the timing determination circuit 1324 shown in FIG. 7 will be described with reference to FIGS. 9 to 11. FIGS. 9 to 11 show an example in which the master clock in which the binary number "true" is continuously superimposed is transmitted from the control unit 21 to the camera unit 13 four times from the beginning. Further, FIGS. 9 to 11 show an example in which a horizontal synchronization signal is input on behalf of the timing determination circuit 1324.

In the operation example described above with reference to FIG. 8, if the horizontal synchronization signal or the vertical synchronization signal changes from the high level to the low level, the timing determination circuit 1324 becomes the high level when the camera clock changes from the low level to the high level (time t21), and outputs an enable signal at the low level after a predetermined time has elapsed (time t31). The operation of the timing determination circuit 1324 in this case is performed normally when, for example, there is a constant relationship between the timing when the horizontal synchronization signal or vertical synchronization signal changes from the high level to the low level and the timing when the camera clock changes from the low level to the high level.

That is, for example, when the timing (time t41) when the horizontal synchronization signal changes from the high level to the low level is earlier than the timing (time t42) when the camera clock changes from the low level to the high level, as shown in FIG. 9, by setting the signal Enable to the high level at the timing (time t42) when the camera clock changes from the low level to the high level, the register control signal can be normally restored from the timing (time t43) when the camera clock next changes from the high level to the low level. In this case, the 4-bit data of "true" at time t43–t44, "true" at time t44–t45, "true" at time t45–t46, and "true" at t46—is correctly restored.

On the other hand, for example, as shown in FIG. 11, when the timing (time t62) when the horizontal synchronization signal changes from the high level to the low level is later than the timing (time t61) when the camera clock changes from the low level to the high level, the signal Enable is set to the high level at the timing (time t64) when the camera clock next changes from the low level to the high level, and when the register control signal is restored from the timing (time t65) when the camera clock next changes from the high level to the low level, the register control signal cannot be restored normally. In this case, the restored data will be incorrect data having four bits of "false" at time t65–t66, "false" at time t66–t67, "false" at t67–t68, and "false" at time t68.

As a countermeasure, for example, the operation of the timing determination circuit 1324 shown in FIG. 7 is modified as follows. That is, in the operation of the timing determination circuit 1324, based on the result of comparing the timing when the horizontal synchronization signal changes from the high level to the low level and the timing when the camera clock changes from the low level to the high level, the timing when the signal Enable is set to the high level is transformed into the following two types.

(1) As shown in FIG. 9, when the timing (time t41) when the horizontal synchronization signal changes from the high level to the low level is earlier than the timing (time t42) when the camera clock changes from the low level to the high level, the signal Enable is set to the high level at the timing (time t42) when the camera clock changes from the low level to the high level.

(2) As shown in FIG. 10, when the timing (time t52) when the horizontal synchronization signal changes from the high level to the low level is later than the timing (time t51) when the camera clock changes from the low level to the high level, the signal Enable is set to the high level at the timing (time t54) when the camera clock changes from the low level to the high level after next.

In the case of (2) above, the first bit of the register control signal (sending) cannot be received, but for example, the data itself can be restored without any problem by setting an appropriate preamble for the register control signal.

As a modification of the operation of the timing determination circuit 1324, for example, a configuration may be adopted in which a clock delayed by a predetermined time (for example, ¼ cycle) from the camera clock is generated and the rising edge of the clock is set to the timing when the signal Enable is the high level.

Figure 12:
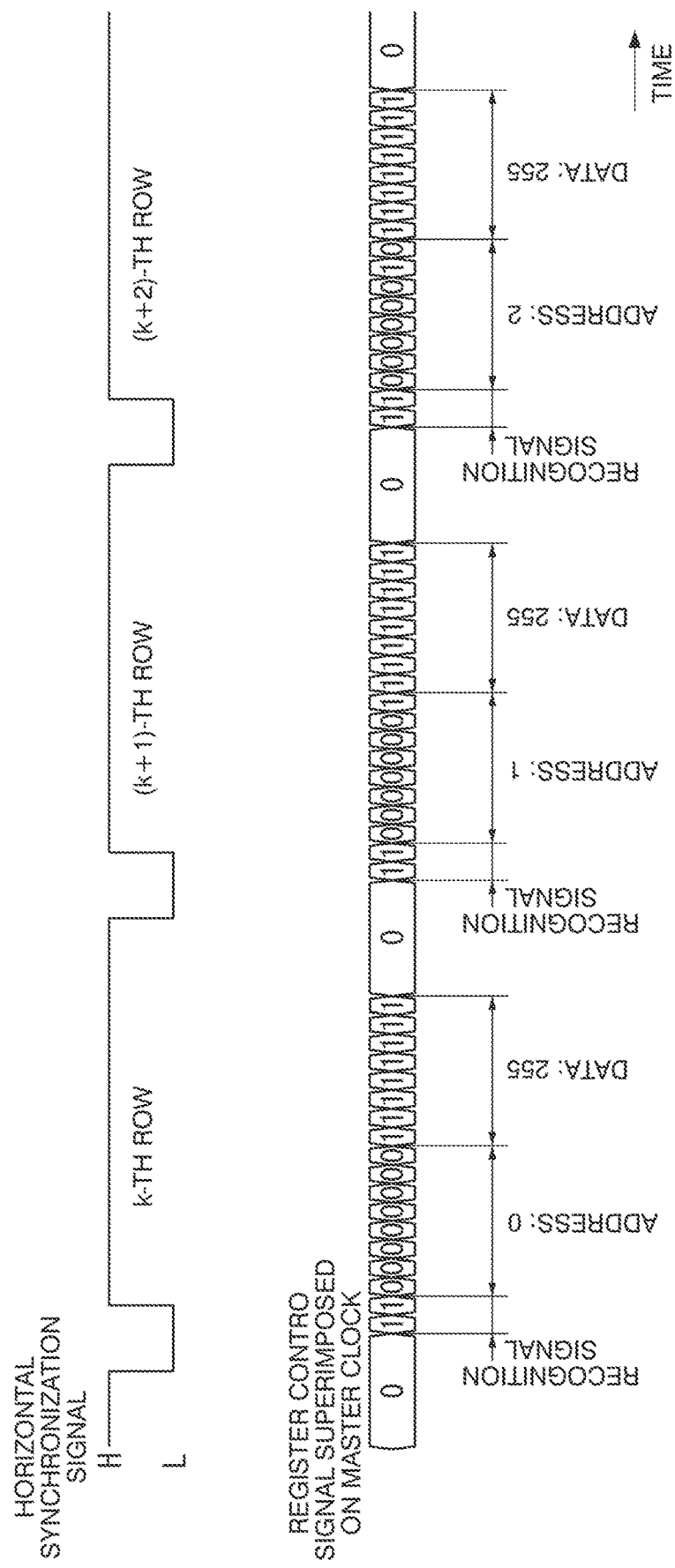
FIG. 12 is a timing chart explaining an operation example of the imaging system 100 shown in FIG. 2.

Next, with reference to FIG. 12, an example of a register-setting signal superimposed on the master clock by the control unit 21 will be described. FIG. 12 is a timing chart explaining an operation example of the imaging system 100 shown in FIG. 2, and shows the time change of the horizontal synchronization signal and the register control signal superimposed on the master clock. The horizontal synchronization signal may be a vertical synchronization signal.

As described above, the master clock generator 212 shown in FIG. 2 sets the timing of the high edge of the master clock to a fixed period, changes whether the timing of the low edge is late or early, that is, whether the duty is small or large for each clock, and superimposes the logic of "true" (="1") or "false" (="0") on the master clock. Here, the clock with a small duty is set to "0", and the clock with a large duty is set to "1". The master clock generator 212 constitutes a register-setting signal with this superimposed signal, and outputs it at a timing synchronized with the horizontal synchronization signal.

For example, assuming that the horizontal blanking period of the horizontal synchronization signal is "L", after the horizontal synchronization signal becomes "L", as the register-setting signals, "1" and "1" (recognition signal)+register address 8 bits+data 8 bits are output, and "0" is output until the output of the next register-setting signal. Then, as shown in FIG. 12, the setting signal of one register can be transmitted to the camera unit 13 side for each line read. In the example shown in FIG. 12, the register-setting signal that sets the data 255 at address 0 on the kth line (k is an integer from 1 to m), the register-setting signal that sets data 255 to address 1 on the k+1th line, and the register-setting signal that sets the data 255 at the address 2 on the k+2nd line are superimposed on the master clock.

As described above, according to the embodiment of the present invention or a modification thereof, the register control signal indicating the imaging condition of the imager 134 can be superimposed on the master clock and transmitted, so that the types of signal lines connecting the camera unit 13 and the control unit 21 can be reduced.

Although the preferred embodiments of the present invention have been described above, the present invention is not limited to these embodiments and variations thereof. It is possible to add, omit, or replace constituent elements, and make other changes to the configuration without departing from the spirit of the present invention. Further, the present invention is not limited by the above description, but only by the scope of the appended claims.

According to the imaging system of each of the above aspects, it is possible to realize line saving of the scope.

What is claimed is:

1. An imaging system, in which a camera unit and a control unit are connected by a video signal transmission line that transmits a video signal from the camera unit to the control unit and a clock line that transmits a master clock from the control unit to the camera unit, and the camera unit and the control unit operate in synchronization with each other by a horizontal synchronization signal and a vertical synchronization signal indicating a reading timing of the video signal,
wherein the camera unit includes
an imager configured to generate the video signal;
a register configured to be capable of writing and setting an imaging condition of the imager;
a camera clock generation circuit configured to synchronize with the master clock and generate a camera clock having a predetermined duty; and
a signal analysis circuit configured to encode information superimposed on the master clock,
the control unit includes a register control signal transmitter configured to change a duty of the master clock based on a timing of the horizontal synchronization signal or the vertical synchronization signal, to superimpose a register control signal, which indicates the imaging condition of the imager on the master clock and transmits it, using a combination of a first signal having a duty shorter than the camera clock and a second signal having a duty longer than the camera clock, and
the signal analysis circuit is configured to encode the register control signal superimposed on the master clock using the camera clock based on the timing of the horizontal synchronization signal or the vertical synchronization signal, and write the imaging condition indicated by the register control signal to the register.

2. The imaging system according to claim 1, wherein a transmission time of a high-level signal and a transmission time of a low-level signal by the first signal and the second signal are substantially the same within a predetermined period.

3. The imaging system according to claim 2, wherein
true and false of binary numbers constituting the register control signal are each represented by a combination of the first signal and the second signal,
a period of the high-level signal and a period of the low-level signal by the first signal and the second signal constituting the true are substantially the same, and
a period of the high-level signal and a period of the low-level signal by the first signal and the second signal constituting the false are substantially the same.

4. The imaging system according to claim 1, wherein the true and false of the binary numbers constituting the register control signal are represented by changing a pair order of the first signal and the second signal.

5. The imaging system according to claim 4, wherein the signal analysis circuit includes a DFF (D flip-flop) circuit configured to determine the high-level signal or the low-level signal of the register control signal superimposed on the master clock at a timing of a falling edge of the camera clock,
a frequency division clock generation circuit configured to divide the camera clock to generate a frequency division clock having a double cycle, and
an FF (flip-flop) circuit configured to determine the pair order of the first signal and the second signal and determine the true or the false, based on the high-level signal or the low-level signal determined by the DFF circuit and the frequency division clock.

6. The imaging system according to claim 1, wherein
the register control signal transmitter is configured to transmit the register control signal to which an error correction code is added, and
the signal analysis circuit is configured to encode the register control signal, and writes the imaging condition indicated by the register control signal, which has been correctly transmitted, to the register based on the error correction code.

7. An endoscope device that includes an imaging system, in which a camera unit and a control unit are connected by a video signal transmission line that transmits a video signal from the camera unit to the control unit and a clock line that transmits a master clock from the control unit to the camera unit, and the camera unit and the control unit operate in synchronization with each other by a horizontal synchronization signal and a vertical synchronization signal indicating a reading timing of the video signal,
wherein the camera unit includes
an imager configured to generate the video signal;
a register configured to be capable of writing and setting an imaging condition of the imager;
a camera clock generation circuit configured to synchronize with the master clock and generate a camera clock having a predetermined duty; and
a signal analysis circuit configured to encode information superimposed on the master clock,
the control unit includes a register control signal transmitter configured to change a duty of the master clock based on a timing of the horizontal synchronization signal or the vertical synchronization signal, to superimpose a register control signal, which indicates the imaging condition of the imager on the master clock and transmits it, using a combination of a first signal having a duty shorter than the camera clock and a second signal having a duty longer than the camera clock,
the signal analysis circuit is configured to encode the register control signal superimposed on the master clock using the camera clock based on the timing of the horizontal synchronization signal or the vertical synchronization signal, and write the imaging condition indicated by the register control signal to the register,
the camera unit is arranged at a distal end of an insertion part, and
the control unit is arranged in a main body.

* * * * *